US010670613B2

(12) United States Patent
Umek et al.

(10) Patent No.: US 10,670,613 B2
(45) Date of Patent: *Jun. 2, 2020

(54) ANTIBODY ARRAY FOR MEASURING A PANEL OF AMYLOIDS

(71) Applicant: Meso Scale Technologies, LLC., Rockville, MD (US)

(72) Inventors: Robert M. Umek, Silver Spring, MD (US); Pankaj Oberoi, Rockville, MD (US)

(73) Assignee: MESO SCALE TECHNOLOGIES, LLC., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/012,992

(22) Filed: Jun. 20, 2018

(65) Prior Publication Data

US 2018/0292419 A1 Oct. 11, 2018

Related U.S. Application Data

(60) Continuation of application No. 15/581,143, filed on Apr. 28, 2017, now Pat. No. 10,024,871, which is a division of application No. 13/721,254, filed on Dec. 20, 2012, now abandoned.

(60) Provisional application No. 61/578,344, filed on Dec. 21, 2011.

(51) Int. Cl.
G01N 33/68 (2006.01)

(52) U.S. Cl.
CPC . *G01N 33/6896* (2013.01); *G01N 2333/4709* (2013.01); *G01N 2800/2821* (2013.01); *G01N 2800/52* (2013.01)

(58) Field of Classification Search
CPC ............. A61K 2039/505; A61K 51/10; G01N 33/6896; G01N 2800/2821; G01N 2333/4709; G01N 2800/52; G01N 33/6854
See application file for complete search history.

(56) References Cited

U.S. PATENT DOCUMENTS

| | | | |
|---|---|---|---|
| 4,168,146 A | 9/1979 | Grubb et al. | |
| 4,235,601 A | 11/1980 | Deutsch et al. | |
| 4,366,241 A | 12/1982 | Tom et al. | |
| 4,442,204 A | 4/1984 | Greenquist et al. | |
| 5,208,535 A | 5/1993 | Nakayama et al. | |
| 5,492,812 A | 2/1996 | Vooheis | |
| 5,807,522 A | 9/1998 | Brown et al. | |
| 6,110,426 A | 8/2000 | Shalon et al. | |
| 6,787,637 B1 | 9/2004 | Schenk | |
| 2003/0113713 A1 | 6/2003 | Glezer et al. | |
| 2003/0207290 A1 | 11/2003 | Kenten et al. | |
| 2004/0022677 A1 | 2/2004 | Wohlstadter et al. | |
| 2004/0189311 A1 | 9/2004 | Glezer et al. | |
| 2005/0052646 A1 | 3/2005 | Wohlstadter et al. | |
| 2005/0142033 A1 | 6/2005 | Glezer et al. | |
| 2006/0205012 A1 | 9/2006 | Debad et al. | |
| 2013/0164217 A1 | 6/2013 | Umek et al. | |
| 2017/0234892 A1 | 8/2017 | Umek et al. | |

FOREIGN PATENT DOCUMENTS

| WO | 99/26067 A1 | 5/1999 |
|---|---|---|
| WO | 2004/058055 A2 | 7/2004 |

OTHER PUBLICATIONS

Andreasen N. et al., "CSF Markers for Alzheimer's Disease: Total Tau, Phospho-Tau and Aβ42", World J. Biol Psychiatry 4:147-155 (2003).
Andreasen N. et al., "Cerebrospinal Fluid Levels of Total-Tau, Phospho-Tau and Aβ42 Predicts Development of Alzheimer's Disease in Patients with Mild Cognitive Impairment", Acta Neurol Scand 107(Suppl. 179):47-51 (2003).
Andreasen N. et al., "Evaluation of CSF-Tau and CSF-Aβ42 as Diagnostic Markers for Alzheimer Disease in Clinical Practice", Arch Neurol 58:373-379 (Mar. 2001).
Berns A., "Gene Expression in Diagnosis", Cancer 403:491-492 (Feb. 3, 2000).
Bishop J.E. et al., "Simultaneous Quantification of Six Human Cytokines in a Single Sample Using Microparticle-Based Flow Cytometric Technology", Clinical Chemistry 45(9):1693-1694 (1999).
Blennow K. et al., "CSF Markers for Incipient Alzheimer's Disease", The Lancet Neurology 2:605-613 (Oct. 2003).
Delehanty J.B., "Printing Functional Protein Microarrays Using Piezoelectric Capillaries", Methods in Molecular Biology 264:135-143 (2004).
Du Y. et al., "Reduced Levels of Amyloid β-Peptide Antibody in Alzheimer's Disease", Neurology 57:801-804 (Sep. 2001).
Ertekin-Taner N. et al., "Heritability of Plasma Amyloid β in Typical Late-Onset Alzheimer's Disease Pedigrees", Genetic Epidemiology 21:19-30 (2001).
Fitzpatrick A.L. et al., "Incidence and Prevalence of Dementia in the Cardiovascular Health Study", J. Am. Geriatr Soc. 52:195-204 (2004).
Flirski M. et al., "Biochemical Markers and Risk Factors of Alzheimer's Disease", Current Alzheimer Research 2:47-64 (2005).
Frank R.A. et al., "Biological Markers for Therapeutic Trials in Alzheimer's Disease Proceedings of the Biological Markers Working Group; NIA Initiative on Neuroimaging in Alzheimer's Disease", Neurobiology of Aging 24:521-536 (2003).
Fukumoto H. et al., "Age But Not Diagnosis is the Main Predictor of Plasma Amyloid β-Protein Levels", Arch Neurol 60:958-964 (Jul. 2003).

(Continued)

*Primary Examiner* — Gregory S Emch
(74) *Attorney, Agent, or Firm* — Scully, Scott, Murphy & Presser, P.C.

(57) ABSTRACT

Described are assay methods, modules and kits useful in the detection, treatment and/or prevention of dementia and related conditions, including but not limited to Alzheimer's disease and mild cognitive disorders.

12 Claims, No Drawings
Specification includes a Sequence Listing.

(56) References Cited

OTHER PUBLICATIONS

Hampel H. et al., "Value of CSF β-Amyloid1-42 and Tau as Predictors of Alzheimer's Disease in Patients with Mild Cognitive Impairment", Molecular Psychiatry 9:705-710 (2004).

Hampel H. et al., "Core Biological Marker Candidates of Alzheimer's Disease-Perspectives for Diagnosis, Prediction of Outcome and Reflection of Biological Activity", Journal of Neural Transmission 111:247-272 (2004).

Herholz K. et al., "Clinical Amyloid Imaging in Alzheimer's Disease", The Lancet Neurology 10:667-670 (Jul. 2011).

Hulstaert F. et al., "Improved Discrimination of AD Patients Using β-Amyloid(1-42) and Tau Levels in CSF", Neurology 52:1555-1562 (1999).

Kapaki E. et al., "Highly Increased CSF Tau Protein and Decreased β-Amyloid (1-42) in Sporadic CJD: a Discrimination from Alzheimer's Disease?", J. Neurol Neurosurg Psychiatry 71:401-403 (2001).

Knopman D.S. et al., "Practice Parameter: Diagnosis of Dementia (An Evidence-Based Review)—Report of the Quality Standards Subcommittee of the American Academy of Neurology", Neurology 56:1143-1153 (2001).

Lewczuk P. et al., "Neurochemical Diagnosis of Alzheimer's Dementia by CSF Aβ42, Aβ42/Aβ40 Ratio and Total Tau", Neurobiology of Aging 25:273-281 (2004).

Lovett R.A., "Toxicogenomics: Toxicologists Brace for Genomics Revolution", Science 289(5479):536-537 (Jul. 28, 2000).

Lue R.Y.P. et al., "Site-Specific Immobilization of Biotinylated Proteins for Protein Microarray Analysis", Methods in Molecular Biology 264:85-100 (2004).

Mayeux R. et al., "Plasma Aβ40 and Aβ42 and Alzheimer's Disease", Neurology 61:1185-1190 (2003).

Minino A.M. et al., "Deaths: Final Data for 2000", National Vital Statistics Reports 50(15):1-119 (Sep. 16, 2002).

Motter R. et al., "Reduction of β-Amyloid Peptide42 in the Cerebrospinal Fluid of Patients with Alzheimer's Disease", Ann Neurol 38:643-648 (1995).

Park M.K. et al., "A Latex Bead-Based Flow Cytometric Immunoassay Capable of Simultaneous Typing of Multiple Pneumococcal Serotypes (Multibead Assay)", Clinical and Diagnostic Laboratory Immunology 7(3):486-489 (May 2000).

Pitschke M. et al., "Detection of Single Amyloid β-Protein Aggregates in the Cerebrospinal Fluid of Alzheimer's Patients by Fluorescence Correlation Spectroscopy", Nature Medicine 4(7):832-834 (Jul. 1998).

Portelius E. et al., "Distinct Cerebrospinal Fluid Amyloid β Peptide Signatures in Sporadic and PSEN1 A431E-Associated Familial Alzheimer's Disease", Molecular Neurodegeneration 5(2):1-10 (2010).

Prince J.A. et al., "APOE ε4 Allele is Associated with Reduced Cerebrospinal Fluid Levels of Aβ42", Neurology 62:2116-2118 (2004).

Riemenschneider M. et al., "Cerebrospinal Fluid Tau and β-Amyloid 42 Proteins Identify Alzheimer Disease in Subjects with Mild Cognitive Impairment", Arch Neurol 59:1729-1734 (Nov. 2002).

The Ronald and Nancy Reagan Research Institute of the Alzheimer's Association and the National Institute on Aging Working Group, "Consensus Report of the Working Group on: Molecular and Biochemical Markers of Alzheimer's Disease", Neurobiology of Aging 19(2):109-116 (1998).

Selkoe D.J., "Alzheimer Disease: Mechanistic Understanding Predicts Novel Therapies", Ann Intern Med. 140:627-638 (2004).

Shoji M. et al., "Combination Assay of CSF Tau, Aβ1-40 and Aβ1-42(43) as a Biochemical Marker of Alzheimer's Disease", Journal of the Neurological Sciences 158:134-140 (1998).

Skates S.J. et al., "Pooling of Case Specimens to Create Standard Serum Sets for Screening Cancer Biomarkers", Cancer Epidemiol Biomarkers Prev. 16(2):334-341 (2007).

Skoog I. et al., "Cerebrospinal Fluid Beta-Amyloid 42 is Reduced Before the Onset of Sporadic Dementia: a Population-Based Study in 85-Year-Olds", Dementia and Geriatric Cognitive Disorders 15:169-176 (2003).

Sobów T. et al., "Amyloid-Beta and Tau Proteins as Biochemical Markers of Alzheimer's Disease", Acta Neurobiol Exp 64:53-70 (2004).

Sobów T. et al., "PD-070 Plasma Amyloid Beta Peptides Levels in Sporadic Alzheimer's Disease and Amnestic Mild Cognitive Impairment", International Psychogeriatrics 15(S2):357 (Aug. 2003).

Strozyk D. et al., "CSF Aβ 42 Levels Correlate with Amyloid-Neuropathology in a Population-Based Autopsy Study", Neurology 60:652-656 (2003).

Sunderland T. et al., "Decreased β-Amyloid1-42 and Increased Tau Levels in Cerebrospinal Fluid of Patients with Alzheimer Disease", JAMA 289(16):2094-2103 (Apr. 2003).

Van Dijk E.J. et al., "Plasma Amyloid β, Apolipoprotein E, Lacunar Infarcts, and White Matter Lesions", Ann Neurol 55:570-575 (2004).

Verbeek MM et al., "Brain-Specific Proteins in Cerebrospinal Fluid for the Diagnosis of Neurodegenerative Diseases", Ann Clin Biochem 40:25-40 (2003).

Vignali D.A.A., "Multiplexed Particle-Based Flow Cytometric Assays", Journal of Immunological Methods 243:243-255 (2000).

Walt D.R., "Molecular Biology: Bead-Based Fiber-Optic Arrays", Science 287(5452):451-452 (Jan. 21, 2000).

U.S. Office Action dated Jun. 2, 2017 received in U.S. Appl. No. 15/581,143.

U.S. Office Action dated Sep. 30, 2016 received in U.S. Appl. No. 13/721,254.

U.S. Final Office Action dated Sep. 28, 2015 received in U.S. Appl. No. 13/721,254.

U.S. Office Action dated Mar. 10, 2015 received in U.S. Appl. No. 13/721,254.

ANTIBODY ARRAY FOR MEASURING A PANEL OF AMYLOIDS

CROSS REFERENCE TO RELATED APPLICATIONS

The present application is a continuation of copending application Ser. No. 15/581,143, filed Apr. 28, 2017, which is a divisional of application Ser. No. 13/721,254, filed on Dec. 20, 2012, now abandoned, which claims the benefit of U.S. Provisional Application No. 61/578,344, filed on Dec. 21, 2011, the entire contents of which are incorporated herein by reference.

FIELD OF THE INVENTION

The invention relates to assay methods, modules and kits for diagnostic assays useful in the detection, treatment and/or prevention of dementia and related conditions, including but not limited to Alzheimer's disease and mild cognitive disorders. In particular, the assays of the invention are useful in the diagnosis, treatment and/or prevention of a disease or condition associated with an abnormal level of one or more isoforms of amyloid beta peptides ("A$\beta$") and/or with a changed ratio of levels of A$\beta$ isoforms and/or with the formation of plaques containing one or more A$\beta$ isoforms in a mammal.

BACKGROUND OF THE INVENTION

Alzheimer's disease is characterized by a gradual loss of memory, decline in the ability to perform routine tasks, disorientation, difficulty in learning, loss of language skills, impaired judgment and ability to plan, and personality changes. Over time, these changes become so severe that they interfere with an individual's daily functioning, resulting eventually in death. Alzheimer's disease is a type of dementia and it is only confirmed upon autopsy when the characteristic plaques and tangles are observed.

Biomarkers that can be used to diagnose Alzheimer's disease and/or other forms of dementia are in demand. Particularly useful are biomarkers that can diagnose Alzheimer's disease with greater than 95% precision and accuracy before autopsy, biomarkers that can distinguish among various forms of dementia, biomarkers that reflect modulation of the disease by therapeutics, and biomarkers that predict the progression of Alzheimer's disease well in advance of neurological symptoms. For example, studies suggest that by the time A$\beta$ 42 or tau are altered in abundance in cerebral spinal fluid, there is already significant neuronal damage in the brain. The hope is that early stage biomarkers can be found to justify prophylactic intervention early in a patient's life.

SUMMARY OF THE INVENTION

The invention provides a method for diagnosing dementia in a patient comprising (a) measuring a level of a first biomarker in a test sample obtained from a patient, wherein said first biomarker is selected from the group consisting of A$\beta$ 16, A$\beta$ 17, and combinations thereof; (b) and diagnosing from said measuring step the presence, absence, and/or progression of dementia in said patient.

Also provided is a method for monitoring the progression of and/or efficacy of treatment for dementia in a patient, said method comprising (a) measuring the level(s) of a first biomarker in samples obtained at different times from said patient, wherein said first biomarker is selected from the group consisting of A$\beta$ 16, A$\beta$ 17, and combinations thereof; and (b) determining from said level(s) of said first biomarker the progression of and/or efficacy of treatment for dementia in said patient.

Still further, the invention provides a method for diagnosing, treating and/or preventing a disease or condition associated with an abnormal level of one or more isoforms of amyloid beta peptides in a patient comprising (a) measuring a level of a first biomarker in a test sample obtained from a patient, wherein said first biomarker is selected from the group consisting of A$\beta$ 16, A$\beta$ 17, and combinations thereof; and (b) diagnosing from said measuring step the presence, absence, and/or progression of said condition in said patient.

The invention contemplates a method for diagnosing, treating and/or preventing a disease or condition associated with an abnormal level of one or more isoforms of amyloid beta peptides, said method comprising (a) measuring the level(s) of a first biomarker in samples obtained at different times from said patient, wherein said first biomarker is selected from the group consisting of A$\beta$ 16, A$\beta$ 17, and combinations thereof; and (b) determining from said level(s) of said first biomarker the progression of and/or efficacy of treatment for said condition in said patient.

Also provided is a method for diagnosing Alzheimer's disease in a patient comprising (a) measuring a level of a first biomarker in a test sample obtained from a patient, wherein said first biomarker is selected from the group consisting of A$\beta$ 16, A$\beta$ 17, and combinations thereof; (b) and diagnosing from said measuring step the presence, absence, and/or progression of Alzheimer's disease in said patient.

And further provided is a method for monitoring the progression of and/or efficacy of treatment for Alzheimer's disease in a patient, said method comprising (a) measuring the level(s) of a first biomarker in samples obtained at different times from said patient, wherein said first biomarker is selected from the group consisting of A$\beta$ 16, A$\beta$ 17, and combinations thereof; and (b) determining from said level(s) of said first biomarker the progression of and/or efficacy of treatment for Alzheimer's disease in said patient.

The methods of the present invention may further include evaluating one or more additional biomarker selected from the group consisting of A$\beta$ 42, A$\beta$ 40, A$\beta$ 38, A$\beta$ 39, A$\beta$ 37, A$\beta$ 34, A$\beta$ 43, tau, fragments and isoforms of A$\beta$ peptides and tau, and combinations thereof.

DESCRIPTION OF SPECIFIC EMBODIMENTS OF THE INVENTION

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The articles "a" and "an" are used herein to refer to one or to more than one (i.e., to at least one) of the grammatical object of the article. By way of example, "an element" means one element or more than one element.

"Dementia" refers to a group of similar age-related disorders that result in diminished cognitive functioning (there are also injury- and AIDS-associated dementia that are not age related). Dementia is usually chronic or progressive in nature and characterized by disturbance of multiple higher cortical functions, including memory, thinking, orientation, comprehension, calculation, learning capacity, language, and judgment. Impairments of cognitive function are commonly accompanied, and occasionally preceded, by deterioration in emotional control, social behavior, or motivation. This syndrome occurs in Alzheimer's disease, in cerebrovascular disease, AIDS, and in other conditions primarily or secondarily affecting the brain (World Health Organization ICD-10, 1992).

Alzheimer's disease is one form of dementia. Like other forms of dementia, diagnosis of Alzheimer's disease is based on clinical and neuropsychological evaluation with the exclusion of secondary causes of memory loss, with final confirmation by autopsy. Like other forms of dementia, Alzheimer's disease progresses through three main stages: mild, moderate, and severe. Neuropsychological symptoms of mild or early stage Alzheimer's disease may include but are not limited to difficulty learning and remembering new information; difficulty managing finances, planning meals, taking medication on schedule; depression symptoms (sadness, decreased interest in usual activities, loss of energy); and disorientation in otherwise familiar places. In moderate Alzheimer's disease, the damaging processes occurring in the brain worsen and spread to other areas that control language, reasoning, sensory processing, and thought. In this stage, neuropsychological symptoms of Alzheimer's disease become more pronounced and behavioral problems may become more obvious; these symptoms include but are not limited to forgetfulness, continually repeating stories and/or asking the same questions repeatedly, difficulty performing routine daily tasks, following written instructions, agitation, restlessness, repetitive movements, wandering, paranoia, delusions, hallucinations, deficits in intellect and reasoning, lack of concern for appearance, hygiene, and sleep become more noticeable. Finally, in the advanced stages of Alzheimer's disease, damage to the brain's nerve cells is widespread. People with severe Alzheimer's may exhibit neuropsychological symptoms may include difficulty walking and communicating coherently, refusal to eat or drink, an inability to recognize family or faces, and difficulty with all essential activities of daily living.

Alzheimer's disease is characterized by two major pathologic observations in the brain: neurofibrillary tangles (NFT) and beta amyloid (or neuritic) plaques, comprised predominantly of an aggregate of amyloid beta (Aβ). Individuals with Alzheimer's disease exhibit characteristic beta-amyloid deposits in the brain (beta amyloid plaques) and in cerebral blood vessels (beta amyloid angiopathy) as well as neurofibrillary tangles. Neurofibrillary tangles occur not only in Alzheimer's disease but also in other dementia-inducing disorders. On autopsy, large numbers of these lesions are generally found in areas of the human brain important for memory and cognition.

Beta-amyloid is a neurotoxic peptide that exists in several isoforms, now believed to be a causative precursor or factor in the development of disease. Deposition of Aβ in areas of the brain responsible for cognitive activities is a major factor in the development of Alzheimer's disease. Beta-amyloid plaques are predominantly composed of amyloid beta peptide. The various fragments of Aβ peptide are derived by sequential proteolysis of the amyloid precursor protein (APP). Several proteases called secretases are involved in the processing of APP. The processing of APP leads to various fragments of Aβ, including but not limited to Aβ 40, Aβ 42, Aβ 39, Aβ 38, Aβ 37, Aβ 43, Aβ 34, Aβ 17, and Aβ 16.

The sequence for human APP is found at GenBank Accession No. XM047793. The sequences of the various preferred isoforms of human Ab are provided in Table 1 below:

TABLE 1

| | |
|---|---|
| Aβ 43 | D-A-E-F-R-H-D-S-G-Y-E-V-H-H-Q-K-L-V-F-F-A-E-D-V-G-S-N-K-G-A-I-I-G-L-M-V-G-G-V-V-I-A-T (SEQ ID NO: 1) |
| Aβ 42 | D-A-E-F-R-H-D-S-G-Y-E-V-H-H-Q-K-L-V-F-F-A-E-D-V-G-S-N-K-G-A-I-I-G-L-M-V-G-G-V-V-I-A (SEQ ID NO: 2) |
| Aβ 40 | D-A-E-F-R-H-D-S-G-Y-E-V-H-H-Q-K-L-V-F-F-A-E-D-V-G-S-N-K-G-A-I-I-G-L-M-V-G-G-V-V (SEQ ID NO: 3) |
| Aβ 39 | D-A-E-F-R-H-D-S-G-Y-E-V-H-H-Q-K-L-V-F-F-A-E-D-V-G-S-N-K-G-A-I-I-G-L-M-V-G-G-V (SEQ ID NO: 4) |
| Aβ 38 | D-A-E-F-R-H-D-S-G-Y-E-V-H-H-Q-K-L-V-F-F-A-E-D-V-G-S-N-K-G-A-I-I-G-L-M-V-G-G (SEQ ID NO: 5) |
| Aβ 37 | D-A-E-F-R-H-D-S-G-Y-E-V-H-H-Q-K-L-V-F-F-A-E-D-V-G-S-N-K-G-A-I-I-G-L-M-V-G (SEQ ID NO: 6) |
| Aβ 34 | D-A-E-F-R-H-D-S-G-Y-E-V-H-H-Q-K-L-V-F-F-A-E-D-V-G-S-N-K-G-A-I-I-G-L (SEQ ID NO: 7) |
| Aβ 17 | D-A-E-F-R-H-D-S-G-Y-E-V-H-H-Q-K-L (SEQ ID NO: 8) |
| Aβ 16 | D-A-E-F-R-H-D-S-G-Y-E-V-H-H-Q-K (SEQ ID NO: 9) |

It will be understood that other isoforms of Aβ are within the scope of the invention, e.g., those isoforms having a C-terminus at position 16, 17, 34, 37, 38, 39, and 40 relative to the numbering for Aβ 1-42 and truncated n-termini.

Cleavage of APP at the N-terminus of the Aβ peptide by beta-secretase (BACE) and at the C-terminus by one or more gamma-secretases constitutes the beta-amyloidogenic pathway, i.e., the pathway by which Aβ is formed. Cleavage of APP by alpha-secretase produces alpha-sAPP, a secreted form of APP that does not result in beta-amyloid plaque formation. This alternate pathway precludes the formation of Aβ peptide.

In addition to the numerous isoforms of Aβ, various proteins have been associated with the diagnosis of dementia or Alzheimer's disease. Table 2 summarizes these markers. (See Flirski et al., Current Alzheimer Research (2005) 2: 47-64, the disclosure of which is incorporated herein by reference in its entirety.)

TABLE 2

| Marker | Sample | Up- or down-regulated in Alzheimer's Patients |
|---|---|---|
| Aβ 42 | CSF | Down |
| Total tau | CSF | Up |
| P-tau | CSF | Up |
| ACT | CSF, plasma | Up |
| F2-iPs | CSF | Up |
| Non-enzymatic antioxidants | Plasma | Down |
| SOD | RBC | Up |
| Cu | Plasma | Up |

TABLE 2-continued

| Marker | Sample | Up- or down-regulated in Alzheimer's Patients |
|---|---|---|
| 24-OHC | CSF | Up |
| NTP | CSF, urine | Up |
| F4-iPs | CSF | Up |
| DNA 8-OHG/free 8-OHG | CSF | Up |
| RNA 8-OHG | CSF | Up |
| 3-nitrotyrosine | CSF | Up |
| tTG | CSF | Up |
| CD95 | Plasma | Up |
| Glyc-AChE | CSF | Up |
| Glyc-BuChE | | |
| ST/PI | CSF | Down |
| hK10 | CSF | Down |
| Aβ3-44/Aβ3-47 | CSF | Down |
| C-tau | CSF | Up |
| Aβ42 | Plasma | Up |
| IL-6, CRP, TNF-alpha | Plasma | Up |
| Haptoglobin, CRP | Plasma | Up |
| TNF-alpha | Plasma | Up |
| antioxidants | Plasma | Up |
| Homocystein | Plasma | Up |
| Folate, vitamin B6, vitamin B12 | Plasma | Down |
| Cholesterol | | Up |
| Lanosterol, lathosterol | | Up |

Therefore, in one embodiment, the invention provides a method for diagnosing Alzheimer's-related dementia and/or plaque formation in the brain of a patient comprising (a) measuring a level of a first biomarker in a test sample obtained from a patient, wherein said first biomarker is selected from the group consisting of Aβ 16 and/or Aβ 17, and combinations thereof; (b) diagnosing from said measuring step the presence, absence, and/or progression of disease (i.e., Alzheimer's-related dementia and/or plaque formation) in said patient. This method may further comprise measuring one or more additional biomarkers, e.g., one or more isoforms of Aβ, total tau, P-tau, C-tau, ACT, F2-iPs, non-enzymatic antioxidants, SOD, Cu, 24-OHC, NTP, F4-iPs, DNA 8-OHG/free 8-OHG, RNA 8-OHG, 3-nitrotyrosine, tTG, CD95, Glyc-AChE, Glyc-BuChE, ST/PI, hK10, IL-6, CRP, TNF-alpha, and combinations thereof. In addition, the present invention also contemplates measuring the level of autoantibodies in a patient sample to a biomarker associated with Alzheimer's-related dementia and/or plaque formation, including but not limited to an Aβ peptide, tau, a fragment or isoform of an Aβ peptide or tau, or combinations thereof. The method can also include measuring autoantibodies to one or more biomarker including but not limited to: Aβ 16, Aβ 17, Aβ 40, Aβ 42, Aβ 39, Aβ 38, Aβ 37, Aβ 34, Aβ 43, total tau, P-tau, C-tau, ACT, F2-iPs, non-enzymatic antioxidants, SOD, Cu, 24-OHC, NTP, DNA 8-OHG/free 8-OHG, RNA 8-OHG, 3-nitrotyrosine, tTG, CD95, Glyc-AChE, Glyc-BuChE, ST/PI, hK10, IL-6, CRP, TNF-alpha, and combinations thereof. The method can include measuring autoantibodies level(s) as well as protein biomarker levels of one or more of the Alzheimer's-related/plaque-related biomarkers identified herein. In addition to measuring protein biomarker and autoantibody levels in a patient sample, the method of the present invention can also include measuring BACE and gamma-secretase activity in a patient sample. In this regard, the patient's profile of autoantibody and biomarker levels, as well as BACE and/or gamma-secretase activities is considered in making a diagnosis of Alzheimer's-related dementia and/or plaque formation, alone or in combination with the clinical evaluation of one or more neuropsychological symptoms listed hereinabove.

In one embodiment, the method comprises measuring Aβ 16 and/or Aβ 17, and one or more of Aβ 40, Aβ 42, Aβ 39, Aβ 38, Aβ 37, Aβ 34, Aβ 43, tau, and combinations thereof. In another embodiment, the method comprises measuring Aβ 16 and/or Aβ 17, and one or more of Aβ 40, Aβ 42, Aβ 38, tau, and combinations thereof. In these embodiments, tau may be total tau, P-tau, C-tau or combinations thereof. Measurements are taken on samples selected from the group consisting of urine, blood and/or cerebrospinal fluid (CSF) and combinations thereof, depending on the biomarker(s) selected.

In addition, the invention provides a method for diagnosing Alzheimer's-related dementia, and/or the development of plaques in the brain of a patient comprising (a) measuring a level of a first biomarker in a test sample obtained from a patient, wherein said first biomarker is selected from the group consisting of Aβ 16 and/or Aβ 17, and combinations thereof; (b) assessing one or more neuropsychological symptoms associated with Alzheimer's-related dementia and/or plaque formation; and (c) diagnosing from said measuring and assessing steps the presence, absence, and/or progression of Alzheimer's-related dementia, and/or plaque formation in said patient. This method may further comprise measuring one or more additional biomarkers, e.g., one or more fragments and/or isoforms of Aβ (Aβ 40, Aβ 42, Aβ 39, Aβ 38, Aβ 37, Aβ 34, Aβ 43), forms of tau (e.g., total tau, P-tau, C-tau, etc.), ACT, F2-iPs, non-enzymatic antioxidants, SOD, Cu, 24-OHC, NTP, F4-iPs, DNA 8-OHG/free 8-OHG, RNA 8-OHG, 3-nitrotyrosine, tTG, CD95, Glyc-AChE, Glyc-BuChE, ST/PI, hK10, IL-6, CRP, TNT-alpha, and combinations thereof, as well as BACE and/or gamma-secretase activity.

In one embodiment, biomarkers of dementia, e.g., Alzheimer's disease, and/or plaque formation reflect a central pathogenic process of the disorder, e.g., degeneration of neurons and synapses or the development of typical lesions as neuritic plaques and neurofibrillary tangles. The biomarkers used in the method of the present invention have a sensitivity of at least 75%, preferably at least 80%, and more preferably at least 85% for detecting Alzheimer's-related dementia, and/or plaque formation, and a specificity of at least 75%, preferably at least 80%, and more preferably at least 85% for distinguishing other dementias. In a preferred embodiment, the biomarkers identified herein can be used to differentiate various stages of Alzheimer's-related dementia and in so doing, can be used to assess a patient's relative progression from one stage of Alzheimer's-related dementia to the next. For example, while CSF Ab42 levels alone can be used to identify the presence of amyloid plaques in asymptomatic patients, evaluation of (i) Aβ42 levels in relation to other isoforms of Aβ, e.g., Aβ 40, Aβ 39, Aβ 38, Aβ 37, Aβ 34, Aβ 43, Aβ16, Aβ17, (ii) Aβ peptide patterns, i.e., the relative levels of each of each individual Aβ peptide and/or the relative ratio of Aβ peptides, preferably measured over time, and/or (iii) Aβ peptide levels in relation to other diagnostic biomarkers, e.g., tau (e.g., p-tau and c-tau), preferably measured over time, can be informative of the disease progression. In a preferred embodiment, disease progression is monitored over time by monitoring biomarker levels at a first time point, t, and repeating that measurement at a second time point, t+n, wherein n is one or more, in order to assess the relative change in the biomarker(s) levels in the patient over a given time interval. The time interval can be measured over the span of hours, days, months, and/or years.

In one embodiment, the biological marker is present in body fluids that are easily accessible, including but not limited to urine, blood or cerebrospinal fluid (CSF). The assays of the present invention may be conducted by any suitable method. In one embodiment, the measuring step is conducted on a single sample, and it may also be conducted in a single assay chamber, including but not limited to a single well of an assay plate. The assay chamber may also be an assay chamber of a cartridge. As used herein, the term "sample" is intended to mean any biological fluid, cell, tissue, organ or combinations or portions thereof, which includes or potentially includes a biomarker of a disease of interest. For example, a sample can be a histologic section of a specimen obtained by biopsy, or cells that are placed in or adapted to tissue culture. A sample further can be a subcellular fraction or extract, or a crude or substantially pure nucleic acid molecule or protein preparation. In one embodiment, the samples that may be analyzed in the assays of the present invention include but are not limited to blood or blood fractions such as, cerebral spinal fluid, serum and plasma. In one embodiment, the level is measured using an immunoassay.

As used herein, a "biomarker" is a substance that is associated with a particular disease. A change in the expression levels of a biomarker may correlate with the risk or progression of a disease or with the susceptibility of the disease to a given treatment. A biomarker may be useful in the diagnosis of disease risk or the presence of disease in an individual, or to tailor treatments for the disease in an individual (choices of drug treatment or administration regimes). In evaluating potential drug therapies, a biomarker may be used as a surrogate for a natural endpoint such as survival or irreversible morbidity. If a treatment alters the biomarker, which has a direct connection to improved health, the biomarker serves as a "surrogate endpoint" for evaluating clinical benefit. A sample that is assayed in the diagnostic methods of the present invention may be obtained from any suitable patient, including but not limited to a patient suspected of having a disorder associated with abnormal Aβ levels, as described herein or a patient having a predisposition to a condition associated with abnormal Aβ levels. The patient may or may not exhibit clinical symptoms associated with a condition associated with abnormal Aβ levels.

As used herein, the term "level" refers to mean the amount, concentration, accumulation or rate of a biomarker molecule. A level can be represented, for example, by the amount or synthesis rate of messenger RNA (mRNA) encoded by a gene, the amount or synthesis rate of polypeptide corresponding to a given amino acid sequence encoded by a gene, or the amount or synthesis rate of a biochemical form of a molecule accumulated in a cell, including, for example, the amount of particular post-synthetic modifications of a molecule such as a polypeptide, nucleic acid or small molecule. The term can be used to refer to an absolute amount of a molecule in a sample or to a relative amount of the molecule, including amounts or concentration determined under steady-state or non-steady-state conditions. Level may also refer to an assay signal that correlates with the amount, concentration, accumulation or rate of a biomarker molecule. The expression level of a molecule can be determined relative to a control molecule in a sample. According to one aspect of the invention, the levels or levels of biomarker(s) are measured in the samples collected from individuals clinically diagnosed with or suspected of or at risk of developing a condition associated with abnormal Aβ levels using conventional methods, e.g., biopsy or other conventional diagnostic methods, as well as from healthy individuals. It may also be used to screen for disease in a broad population of asymptomatic individuals. For example, specific biomarkers valuable in distinguishing between normal and diseased patients could be identified by visual inspection of the data, for example, data plotted on a one-dimensional or multidimensional graph, or using methods of statistical analysis, such as a statistically weighted difference between control individuals and diseased patients and/or Receiver Operating Characteristic (ROC) curve analysis.

For example and without limitation, diagnostically valuable biomarkers may be first identified using a statistically weighted difference between control individuals and diseased patients, calculated as $$\frac{D-N}{\sqrt{\sigma_D * \sigma_N}}$$

wherein D is the median level of a biomarker in patients diagnosed as having, for example, breast cancer or ovarian cancer, N is the median of the control individuals, (TD is the standard deviation of D and (TN is the standard deviation of N. The larger the magnitude, the greater the statistical difference between the diseased and normal populations.

According to one embodiment of the invention, biomarkers resulting in a statistically weighted difference between control individuals and diseased patients of greater than, e.g., 1, 15, 2, 2.5 or 3 could be identified as diagnostically valuable markers.

Another method of statistical analysis for identifying biomarkers is the use of z scores, e.g., as described in Skates et al. (2007) Cancer Epidemiol. Biomarkers Prev. 16(2)334-341. Another method of statistical analysis that can be useful in the inventive methods of the invention for determining the efficacy of particular candidate analytes, such as particular biomarkers, for acting as diagnostic marker(s) is ROC curve analysis. An ROC curve is a graphical approach to looking at the effect of a cut-off criterion, e.g., a cut-off value for a diagnostic indicator such as an assay signal or the level or level of an analyte in a sample, on the ability of a diagnostic to correctly identify positive or negative samples or subjects. One axis of the ROC curve is the true positive rate (TPR, the probability that a true positive sample/subject will be correctly identified as positive, or alternatively, the false negative rate (FNR=1−TPR, the probability that a true positive sample/subject will be incorrectly identified as a negative). The other axis is the true negative rate, i.e., TNR, the probability that a true negative sample will be correctly identified as a negative, or alternatively, the false positive rate (FPR=1−TNR, the probability that a true negative sample will be incorrectly identified as positive). The ROC curve is generated using assay results for a population of samples/subjects by varying the diagnostic cut-off value used to identify samples/subjects as positive or negative and plotting calculated values of TPR or FNR and TNR or FPR for each cut-off value. The area under the curve (referred to herein as the ROC area) is one indication of the ability of the diagnostic to separate positive and negative samples/subjects.

Diagnostic indicators analyzed by ROC curve analysis may be a level or levels of an analyte, e.g., a biomarker, or an assay signal. Alternatively, the diagnostic indicator may be a function of multiple measured values, for example, a function of the level/assay signal of a plurality of analytes, e.g, a plurality of biomarkers, or a function that combines the level or level or assay signal of one or more analytes with a patients scoring value that is determined based on visual, radiological and/or histological evaluation of a patient. The multi-parameter analysis may provide more accurate diagnosis relative to analysis of a single marker.

Candidates for a multi-analyte panel could be selected by using criteria such as individual analyte ROC areas, median difference between groups normalized by geometric interquartile range (IQR) etc. The objective is to partition the analyte space so as to improve separation between groups (for example, normal and disease populations) or to minimize the misclassification rate.

One approach is to define a panel response as a weighted combination of individual analytes and then compute an objective function like ROC area, product of sensitivity and specificity, etc. See e.g., WO 2004/058055, as well as U.S. 2006/0205012, the disclosures of which are incorporated herein by reference in their entireties.

Biomarker levels may be measured using any of a number of techniques available to the person of ordinary skill in the art, e.g., direct physical measurements (e.g., mass spectrometry) or binding assays (e.g., immunoassays, agglutination assays and immunochromatographic assays). The method may also comprise measuring a signal that results from a chemical reactions, e.g., a change in optical absorbance, a change in fluorescence, the generation of chemiluminescence or electrochemiluminescence, a change in reflectivity, refractive index or light scattering, the accumulation or release of detectable labels from the surface, the oxidation or reduction or redox species, an electrical current or potential, changes in magnetic fields, etc. Suitable detection techniques may detect binding events by measuring the participation of labeled binding reagents through the measurement of the labels via their photoluminescence (e.g., via measurement of fluorescence, time-resolved fluorescence, evanescent wave fluorescence, up-converting phosphors, multi-photon fluorescence, etc.), chemiluminescence, electrochemiluminescence, light scattering, optical absorbance, radioactivity, magnetic fields, enzymatic activity (e.g., by measuring enzyme activity through enzymatic reactions that cause changes in optical absorbance or fluorescence or cause the emission of chemiluminescence). Alternatively, detection techniques may be used that do not require the use of labels, e.g., techniques based on measuring mass (e.g., surface acoustic wave measurements), refractive index (e.g., surface plasmon resonance measurements), or the inherent luminescence of an analyte.

Binding assays for measuring biomarker levels may use solid phase or homogenous formats. Suitable assay methods include sandwich or competitive binding assays, Examples of sandwich immunoassays are described in U.S. Pat. Nos. 4,168,146 and 4,366,241, both of which are incorporated herein by reference in their entireties. Examples of competitive immunoassays include those disclosed in U.S. Pat. Nos. 4,235,601, 4,442,204 and 5,208,535, each of which are incorporated herein by reference in their entireties.

Multiple biomarkers may be measured using a multiplexed assay format, e.g., multiplexing through the use of binding reagent arrays, multiplexing using spectral discrimination of labels, multiplexing of flow cytometric analysis of binding assays carried out on particles, e.g., using the Luminex® system. Suitable multiplexing methods include array based binding assays using patterned arrays of immobilized antibodies directed against the biomarkers of interest. Various approaches for conducting multiplexed assays have been described (See e.g., U.S. 20040022677; U.S. 20050052646; U.S. 20030207290; U.S. 20030113713; U.S. 20050142033; and U.S. 20040189311, each of which is incorporated herein by reference in their entireties. One approach to multiplexing binding assays involves the use of patterned arrays of binding reagents, e.g., U.S. Pat. Nos. 5,807,522 and 6,110,426; Delehanty J-B., Printing functional protein microarrays using piezoelectric capillaries, Methods Mol. Biol. (2004) 264: 135-43; Lue R Y et al., Site-specific immobilization of biotinylated proteins for protein microarray analysis, Methods Mol. Biol. (2004) 264: 85-100; Lovett, Toxicogenomics: Toxicologists Brace for Genomics Revolution, Science (2000) 289: 536-537; Berns A, Cancer: Gene expression in diagnosis, nature (2000) 403: 491-92; Walt, Molecular Biology: Bead-based Fiber-Optic Arrays, Science (2000) 287: 451-52 for more details). Another approach involves the use of binding reagents coated on beads that can be individually identified and interrogated. See e.g., WO 9926067, which describes the use of magnetic particles that vary in size to assay multiple analytes; particles belonging to different distinct size ranges are used to assay different analytes. The particles are designed to be distinguished and individually interrogated by flow cytometry. Vignali has described a multiplex binding assay in which 64 different bead sets of microparticles are employed, each having a uniform and distinct proportion of two dyes (Vignali, D. A A, "Multiplexed Particle-Based Flow Cytometric Assays" J. ImmunoL Meth. (2000) 243: 243-55). A similar approach involving a set of 15 different beads of differing size and fluorescence has been disclosed as useful for simultaneous typing of multiple pneumococcal serotypes (Park, M. K et al., "A Latex Bead-Based Flow Cytometric Immunoassay Capable of Simultaneous Typing of Multiple Pneumococcal Serotypes (Multibead Assay)" Clin. Diagn. Lab Immunol. (2000) 7: 486-89, Bishop, J E et al. have described a multiplex sandwich assay for simultaneous quantification of six human cytokines (Bishop, L E. et al., "Simultaneous Quantification of Six Human Cytokines in a Single Sample Using Microparticle-based Flow Cytometric Technology," Clin. Chem (1999) 45:1693-1694. A diagnostic test may be conducted in a single assay chamber, such as a single well of an assay plate or an assay chamber that is an assay chamber of a cartridge.

The assay modules, e.g., assay plates or cartridges or multi-well assay plates), methods and apparatuses for conducting assay measurements suitable for the present invention are described for example, in U.S. 20040022677; U.S. 20050052646; U.S. 20050142033; U.S. 20040189311, each of which is incorporated herein by reference in their entireties. Assay plates and plate readers are now commercially available (MULTI-SPOT® and MULTI-ARRAY® plates and SECTOR® instruments, Meso Scale Discovery, a division of Meso Scale Diagnostics, LLC, Gaithersburg, Md.). In addition, the various isoforms of Aβ can be purchased from AnaSpec, Inc. (www.anaspec.com, Fremont, Calif.) or rPeptide (www.rpeptide.com, Bogart, Ga.). Antibodies specific for the various isoforms of A-beta may be produced by methods known in the art, e.g., Sambrook et al., Molecular Cloning: A Laboratory Manual. (Third Ed.) (2000).

Briefly, mice are immunized with short peptides (7-9 amino acids) corresponding to the c-terminal sequences of A-beta 16, 17, 34, 37, 38, 39, 40, 42, or 43 coupled to KLH. After fusion of spleens, hybridomas are selected after analysis of binding activities against a multiplex array of amyloid peptide fragments. Specifically, A-beta 1-16, 1-17, 1-34, 1-37, 1-38, 1-39, 1-40, 1-42, and 1-43 are immobilized on independent electrodes in a Multi-Spot plate. Supernatants from individual hybridoma clones are introduced into wells containing the peptides arrayed at the bottom. Antibody binding is detected through the use of a labeled goat-antimouse antibody. Hybridomas are selected that exhibit a high signal on only one of the peptides consistent with the production of antibodies that bind well but with specificity for each unique end. For each isoform, hybridomas are identified that bind each of the peptides and not the other forms. In one embodiment, the immunogens that may be used to produce antibodies specific for A-beta 38, -40, and -42 are: 38: CIIGLMVGG (SEQ ID NO: 10); 40: CGLMVGGVV (SEQ ID NO: 11); and 42: LMVGGVVIA (SEQ ID NO: 12), respectively.

Patents, patent applications, publications, and test methods cited in this disclosure are incorporated herein by reference in their entirety.

The present invention is not to be limited in scope by the specific embodiments described herein. Indeed, various modifications of the invention in addition to those described herein will become apparent to those skilled in the art from the foregoing description and accompanying drawings. Such modifications are intended to fall within the scope of the claims.

A claim which recites "comprising" allows the inclusion of other elements to be within the scope of the claim; the invention is also described by such claims reciting the transitional phrases "consisting essentially of" (i.e., allowing the inclusion of other elements to be within the scope of the claim if they do not materially affect operation of the invention) or "consisting of" (i.e., allowing only the elements listed in the claim other than impurities or inconsequential activities which are ordinarily associated with the invention) instead of the "comprising" term. Any of these three transitions can be used to claim the invention.

REFERENCES

1. Fitzpatrick A L, Kuller L H, Ives D G, Lopez O L, Jagust W, Breitner J C, et al. Incidence and prevalence of dementia in the Cardiovascular Health Study. J Am Geriatr Soc 52: 195-204 (2004).
2. Minino A M, Arias E, Kochanek K D, Murphy S L and Smith B L. Deaths: final data for 2000. Natl. Vital Stat Rep 50: 1-119 (2002).
3. Knopman D S, DeKosky S T, Cummings J L, Chui H, Corey-Bloom J, Relkin N, et al. Practice parameter: diagnosis of dementia (an evidence-based review). Report of the Quality Standards Subcommittee of the American Academy of Neurology. Neurology 56: 1143-1153 (2001).
4. The Ronald and Nancy Reagan Research Institute of the Alzheimer's Association and the National Institute on Aging Working Group: Consensus Report of the Working Group on Molecular and Biochemical Markers for Alzheimer's disease. Neurobiol Aging 1998; 19: 109-16.
5. Frank R A, Galasko Hampel H, Hardy J, de Leon M J, Mehta P D, et al. Biological markers for therapeutic trials in Alzheimer's disease. Proceedings of the biological markers working group; NIA initiative on neuroimaging in Alzheimer's disease. Neurobiol Aging 24: 521-536 (2003).
6. Sobow T, Flirski M and Liberski P P. Amyloid-beta and tau proteins as biochemical markers of Alzheimer's disease. Acta Neurobiol Exp 64: 53-70 (2004) Available online at: http://www.nencki.gov.pl/pdf/an/vol64/sobow.pdf.
7. Andreasen N, Sjogren M and Blennow K. CSF markers for Alzheimer's disease: total tau, phospho-tau and A~42. World J Biol Psychiatry 4: 147-155 (2003).
8. Hampel H, Mitchell A, Blennow K, Frank R A, Brettschneider S, Weller L, et al. Core biological marker candidates of Alzheimer's disease—perspectives for diagnosis, prediction of outcome and reflection of biological activity. J Neural Transm 111: 247-272 (2004).
9. Blennow K and Hampel H. CSF markers for incipient Alzheimer's disease. Lancet Neuro 12: 605-613 (2003).
10. Verbeek M M, de Jong D and Kremer H P H. Brain-specific proteins in cerebrospinal fluid for the diagnosis of neurodegenerative diseases. Ann Clin Biochem 40: 25-40 (2003).
11. Selkoe D J. Alzheimer disease: mechanistic understanding predicts novel therapies. Ann Intern Med 140: 627-638 (2004).
12. Matter R, Vigo-Pelfrey C, Kholodenko D, Barbour R, Johnson Wood K, Galasko D, et al. Reduction of amyloid peptide 42 in the cerebrospinal fluid of patients with Alzheimer's disease. Ann Neurol 38: 643-648 (1995).
13. Hulstaert F, Blennow K, Ivanoiu A, Schoonderwaldt H C, Riemenschneider M, De Deyn P P, et al. Improved discrimination of AD patients using beta-amyloid (1-42) and tau levels in CSF. Neurology 52: 1555-1562 (1999).
14. Andreasen N, Minthon L, Davidsson P, Vanmechelen E, Vanderstichele H, Winblad B, et al. Evaluation of CSF-tau and CSF-Aβ42 as diagnostic markers for Alzheimer disease in clinical practice. Arch Neurol 58: 373-379 (2001).
15. Sunderland T, Linker G, Mirza N, Putnam K T, Friedman D L, Kimmel L H, et al. JAMA 289: 2094-2103 (2003).
16. Lewczuk P, Esselmann H, Otto M, Maler J M, Henkel A W, Henkel M K, et al. Neurochemical diagnosis of Alzheimer's dementia by CSF Abeta42, Abeta42/Abeta40 ratio and total tau. Neurobiol Aging 25: 273-281 (2004).
17. Pitschke M., Prior R., Haupt M and Riesner D. Detection of single amyloid beta-protein aggregates in the cerebrospinal fluid of Alzheimer's patients by fluorescence correlation spectroscopy. Nat Med 4: 832-834 (1998).
18. Kapaki E, Kilidireas K and Paraskevas G P. Highly increased CSF tau protein and decreased~-amyloid (1-42) in sporadic CJD: a discrimination from Alzheimer's disease? J Neurol Neurosurg Psychiatry 71: 401-403 (2001).
19. Strozyk D, Blennow K, White L R and Launer L J. CSF Abeta 42 levels correlate with amyloid-neuropathology in a population-based autopsy study. Neurology 60: 652-656 (2003).
20. Riemenschneider M, Lautenschlager N, Wagenpfeil S, Diehl J, Drzezga A and Kurz A. Cerebrospinal fluid tau and β-amyloid 42 proteins identify Alzheimer disease in subjects with mild cognitive impairment. Arch Neurol 59: 1729-1734 (2002).
21. Andreasen N, Vanmechelen E, Vanderstichele H, Davidsson P and Blennow K. Cerebrospinal fluid levels of total-tau, phospho-tau and Abeta42 predicts development of Alzheimer's disease in patients with mild cognitive impairment. Acta Neurol Scand 107: 47-51 (2003).
22. Hampel H, Teipel S J, Fuchsberger T, Andreasen N, Wiltfang J, Otto M, et al. Value of CSF beta-amyloid (1-42) and tau as predictors of Alzheimer's disease in patients with mild cognitive impairment. Mol Psychiatry Dec. 30, 2003.
23. Skoog I, Davidsson P, Aevarsson O, Vanderstichele H, Vanmechelen E and Blennow K. Cerebrospinal fluid beta-amyloid 42 is reduced before the onset of sporadic dementia: a population-based study in 85-year-olds. Dement Geriatr Cogn Disord 15: 169176 (2003).
24. Prince J A, Zetterberg H, Andreasen N, Marcusson J and Blennow K. Neurology 62: 2116-2118 (2004).

25. Shoji M, Matsubara E, Kanai M, Watanabe M, Nakamura T, Tomidokoro Y, et al. Combination assay of CSF tau, Abeta 1-40, and Abeta 1-42(43) as a biochemical marker of Alzheimer's disease. J Neurol Sci 158: 134-140 (1998).
26. Fukumoto H, Tennis M, Locascio J J, Hyman B T, Growdon J H and Irizarry M C. Age but not diagnosis is the main predictor of plasma amyloid β-protein levels. Arch Neurol 60: 958-964 (2003).
27. Ertekin-Taner N, Graff-Radford N, Younkin L H, Eckman C, Adamson J, Schaid D J, et al. Heritability of plasma amyloid beta in typical late-onset Alzheimer's disease pedigrees. Genet Epidemiol 21: 19-30 (2001).
28. Mayeux R, Honig L S, Tang M X, Manly J, Stern Y, Schupf N, et al. Neurology 61: 1185-1190 (2003).
29. Sobow T and Kloszewska I. Plasma amyloid beta peptides levels in sporadic Alzheimer's disease and amnestic mild cognitive impairment. Int Psychogeriatr 15(S2): 357 (2003).
30. van Dijk E J, Prins N D, Vermeer S E, Hofman A, van Duijn C M, Koudstaal P J, et al. Plasma amyloid beta, apolipoprotein E, lacunar infarcts, and white matter lesions. Ann Neurol 55: 570-575 (2004).

---

The invention claimed is:

1. A method for diagnosing Alzheimer's-related dementia in a patient comprising:
 (a) obtaining a test sample from a patient;
 (b) measuring the levels of each biomarker of a panel in said test sample, the panel comprising Aβ 16, Aβ 17, Aβ 42, Aβ 40, Aβ 38, total tau, P-tau, and C-tau;
 (c) conducting a PET scan of said patient's brain using a radioactive diagnostic agent to estimate plaque density in said patient;
 (d) diagnosing from said measuring step and said estimation of plaque density the presence, and/or progression of Alzheimer's-related dementia in said patient; and
 (e) administering a treatment regimen.

2. The method of claim 1 wherein said method further comprises measuring a level of at least one additional biomarker in said sample and determining from said level of said first biomarker and said level of said at least one additional biomarker the presence, and/or progression of Alzheimer's-related dementia in said patient.

3. The method of claim 2 wherein said method further comprises comparing said level of each biomarker of the panel and said at least one additional biomarker(s) in said sample to a level of each biomarker of the panel and said at least one additional biomarker(s) in a normal control sample and diagnosing the presence, and/or progression of Alzheimer's-related dementia in said patient based on said comparison.

4. The method of claim 2 wherein said at least one additional biomarker comprises Aγ 39, Aβ 37, Aβ 34, Aβ 43, or combinations thereof.

5. The method of claim 1 wherein said radioactive diagnostic agent is AMYVID™ (Florbetapir), Pittsburgh Compound B, or combinations thereof.

6. A method for monitoring the disease progression of and/or efficacy of a first treatment regimen for Alzheimer's-related dementia in a patient, said method comprising:
   (a) obtaining two or more test samples from a patient undergoing said first treatment regimen for Alzheimer's-related dementia, wherein said two or more test samples include (i) a first test sample obtained from said patient at time t and (ii) at least one additional test sample obtained at time (t+n), wherein n is an integer greater than 1;
   (b) measuring the level(s) of each biomarker of a panel in said two or more test samples, the panel comprising Aβ 16, Aβ 17, Aβ 42, Aβ 40, Aβ 38, total tau, P-tau, and C-tau;
   (c) conducting a PET scan of said patient's brain using a radioactive diagnostic agent to estimate plaque density in said patient;
   (d) determining from said level(s) of said panel of biomarkers and said estimation of plaque density the progression of and/or efficacy of said first treatment regimen in said patient; and
   (e) administering a second treatment regimen, which is the same as, or different from, the first treatment regimen.

7. The method of claim 6 wherein said method further comprises measuring a level of at least one additional biomarker in said two or more test samples and determining from said level(s) of said first biomarker and said at least one additional biomarker the disease progression and/or efficacy of said first treatment regimen for Alzheimer's-related dementia in said patient.

8. The method of claim 7 wherein said method further comprises comparing said level(s) of each biomarker of the panel and said at least one additional biomarker(s) in said two or more test samples to a level(s) of each biomarker of the panel and said at least one additional biomarker(s) in a normal control sample and determining said disease progression and/or treatment efficacy based on said comparison.

9. The method of claim 7 wherein said at least one additional biomarker comprises Aβ 39, Aβ 37, Aβ 34, Aβ 43, or combinations thereof.

10. The method of claim 7 wherein said radioactive diagnostic agent is AMYVID™ (Florbetapir), Pittsburgh Compound B, or combinations thereof.

11. A method for detecting plaques in the brain of a patient, said method comprising:
   (a) obtaining two or more test samples from a patient undergoing a first treatment regimen for dementia, wherein said two or more test samples include (i) a first test sample obtained from said patient at time t and (ii) at least one additional test sample obtained at time (t+n), wherein n is an integer greater than 1;
   (b) measuring the level(s) of each biomarker of a panel in said two or more test samples, the panel comprising Aβ 16, Aβ 17, Aβ 42, Aβ 40, Aβ 38, Aβ 39, Aβ 37, Aβ 34, Aβ 43, total tau, P-tau, and C-tau;
   (c) conducting a PET scan of said patient's brain using a radioactive diagnostic agent;
   (d) determining from said level(s) of said panel of biomarkers and said PET scan the presence of plaques in the brain of said patient; and
   (e) administering a second treatment regimen, which is the same as, or different from, the first treatment regimen.

12. The method of claim 11 wherein said method further comprises comparing said level(s) of each biomarker of said panel of biomarkers in said two or more test samples to a level of each of said biomarker in said panel of biomarkers in a normal control sample and determining the presence of plaques in the brain of said patient based on said comparison.

* * * * *

SEQUENCE LISTING

```
<160> NUMBER OF SEQ ID NOS: 12

<210> SEQ ID NO 1
<211> LENGTH: 43
<212> TYPE: PRT
<213> ORGANISM: Artificial Sequence
<220> FEATURE:
<223> OTHER INFORMATION: isoforms of human A beta 43

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr
        35                  40

<210> SEQ ID NO 2
<211> LENGTH: 42
<212> TYPE: PRT
<213> ORGANISM: Artificial Sequence
<220> FEATURE:
<223> OTHER INFORMATION: isoforms of human A beta 42

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 3
<211> LENGTH: 40
<212> TYPE: PRT
<213> ORGANISM: Artificial Sequence
<220> FEATURE:
<223> OTHER INFORMATION: isoforms of human A beta 40

<400> SEQUENCE: 3

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 4
<211> LENGTH: 39
<212> TYPE: PRT
```

```
<213> ORGANISM: Artificial Sequence
<220> FEATURE:
<223> OTHER INFORMATION: isoforms of human A beta 39

<400> SEQUENCE: 4

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val
        35

<210> SEQ ID NO 5
<211> LENGTH: 38
<212> TYPE: PRT
<213> ORGANISM: Artificial Sequence
<220> FEATURE:
<223> OTHER INFORMATION: isoforms of human A beta 38

<400> SEQUENCE: 5

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly
        35

<210> SEQ ID NO 6
<211> LENGTH: 37
<212> TYPE: PRT
<213> ORGANISM: Artificial Sequence
<220> FEATURE:
<223> OTHER INFORMATION: isoforms of human A beta 37

<400> SEQUENCE: 6

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly
        35

<210> SEQ ID NO 7
<211> LENGTH: 34
<212> TYPE: PRT
<213> ORGANISM: Artificial Sequence
<220> FEATURE:
<223> OTHER INFORMATION: isoforms of human A beta 34

<400> SEQUENCE: 7

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu

<210> SEQ ID NO 8
<211> LENGTH: 17
<212> TYPE: PRT
<213> ORGANISM: Artificial Sequence
<220> FEATURE:
<223> OTHER INFORMATION: isoforms of human A beta 17
```

```
<400> SEQUENCE: 8

Asp Ala Glu Phe Arg His Asp Ser Gly Tyr Glu Val His His Gln Lys
1               5                   10                  15

Leu

<210> SEQ ID NO 9
<211> LENGTH: 16
<212> TYPE: PRT
<213> ORGANISM: Artificial Sequence
<220> FEATURE:
<223> OTHER INFORMATION: isoforms of human A beta 16

<400> SEQUENCE: 9

Asp Ala Glu Phe Arg His Asp Ser Gly Tyr Glu Val His His Gln Lys
1               5                   10                  15

<210> SEQ ID NO 10
<211> LENGTH: 9
<212> TYPE: PRT
<213> ORGANISM: Artificial Sequence
<220> FEATURE:
<223> OTHER INFORMATION: isoforms of human A beta 38

<400> SEQUENCE: 10

Cys Ile Ile Gly Leu Met Val Gly Gly
1               5

<210> SEQ ID NO 11
<211> LENGTH: 9
<212> TYPE: PRT
<213> ORGANISM: Artificial Sequence
<220> FEATURE:
<223> OTHER INFORMATION: isoforms of human A beta 40

<400> SEQUENCE: 11

Cys Gly Leu Met Val Gly Gly Val Val
1               5

<210> SEQ ID NO 12
<211> LENGTH: 9
<212> TYPE: PRT
<213> ORGANISM: Artificial Sequence
<220> FEATURE:
<223> OTHER INFORMATION: isoforms of human A beta 42

<400> SEQUENCE: 12

Leu Met Val Gly Gly Val Val Ile Ala
1               5
```